United States Patent [19]

Tiep

[11] 4,180,059
[45] Dec. 25, 1979

[54] METHOD OF MEASURING INTRATHORACIC PRESSURE

[75] Inventor: Brian L. Tiep, Monrovia, Calif.

[73] Assignee: City of Hope National Medical Center, Duarte, Calif.

[21] Appl. No.: 874,909

[22] Filed: Feb. 3, 1978

[51] Int. Cl.² ............................................. A61B 5/00
[52] U.S. Cl. .................................... 128/721; 128/748; 128/782
[58] Field of Search ....................... 128/2 R, 2 S, 2.08

[56] References Cited

U.S. PATENT DOCUMENTS

| 3,745,989 | 7/1973 | Pinna | 128/2 R |
| 3,782,188 | 1/1974 | Korber et al. | 128/2 S X |
| 3,820,529 | 6/1974 | Gause et al. | 128/782 |

FOREIGN PATENT DOCUMENTS 790091  9/1935  France ...................................... 128/2 S

OTHER PUBLICATIONS

Bevan et al., Proceed. of the Physiological Society, May, 1971, pp. 10p & 11p.

*Primary Examiner*—Kyle L. Howell
*Attorney, Agent, or Firm*—Edward D. O'Brian

[57] ABSTRACT

A measurement corresponding to the intrathoracic pressure within the body of an individual can be obtained through the use of a transducer. The transducer used includes a movable actuator and is held with reference to the body so that the actuator engages the soft tissue above the suprasternal notch of the individual. As the transducer is located in this manner the actuator moves in accordance with the movement of such tissue as the individual breathes. As a consequence of the operation of the transducer during such movement of the actuator an electric signal is obtained which corresponds to the individual's intrathoracic pressure. An appropriate conventional circuit may be used to indicate such pressure.

2 Claims, 1 Drawing Figure

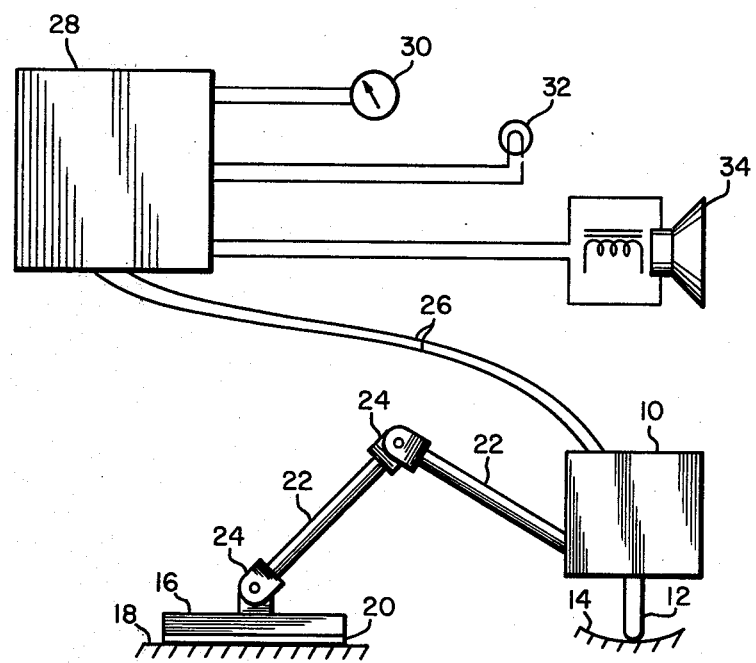

METHOD OF MEASURING INTRATHORACIC PRESSURE

CROSS-REFERENCE TO RELATED APPLICATIONS

The subject matter of this application is related to the Brian L. Tiep application Ser. No. 874,908, filed Feb. 3, 1978, because this copending application discloses and claims a transducer which is considered to be preferable for practicing the method set forth and claimed in this application. The disclosure of this application is incorporated herein by reference.

BACKGROUND OF THE INVENTION

The invention set forth in this specification pertains to a new and improved method of measuring intrathoracic pressure by obtaining a measurement corresponding to the intrathoracic pressure through the use of a transducer.

It is a matter of common knowledge that the measurement of the intrathoracic pressure is important in connection with the treatment of individuals suffering from obstructive lung ailments or problems such as emphysema, bronchiectasis, chronic bronchitis, asthma or the like. Such information as to the intrathoracic pressure of an individual is utilized by a physician in connection with the treatment of such an individual. Continuing information as to the intrathoracic pressure can also be utilized directly by an individual in accordance with various biofeedback techniques so that such an individual can learn to control various aspects of body operation such as, for example, heart performance in alleviating the consequences of such obstructive lung ailments.

It is considered that past techniques of measuring intrathoracic pressure are comparatively undesirable for various reasons which depend on the nature of the technique employed. One such technique has required the use of an esophageal balloon; another has involved the use of a transducer located in the pleural space or cavity of the body. The use of an esophageal balloon is probably the most common of these techniques.

The use of such a balloon can be described as most undesirable. It is difficult to insert such a balloon into the esophagus. Depending upon the physical condition of the patient the use of such a balloon may be comparatively dangerous. It is also most uncomfortable for an individual to have such a balloon located within his or her body. The use of a transducer within the pleural space is "difficult" and undesirable because of problems in connection with the insertion of a transducer in such a space.

SUMMARY OF THE INVENTION

As a result of these considerations it is considered that there is a need for a new and improved method of obtaining a measurement indicating or corresponding to intrathoracic pressure. For convenience such a measurement can be indicated as a measurement of intrathoracic pressure. A basic or broad objective of the present invention is to fulfill this need. A further objective of the invention is to provide a method for measuring intrathoracic pressure which may be easily and conveniently carried out without any significant discomfort to an individual and without inserting any sort of device within the body.

In accordance with this invention these objectives are achieved by providing a method of obtaining a measurement corresponding to the intrathoracic pressure within the body of an individual which comprises the steps of: locating a movable actuator of a transducer against the soft tissue of the suprasternal notch in a position in which variation in the surface tension of the skin occurring during breathing will be transmitted to the actuator of the transducer; allowing the individual to breathe; and monitoring the output of the transducer so as to obtain an output which corresponds to the intrathoracic pressure of the individual as the individual breathes.

BRIEF DESCRIPTION OF THE DRAWING

Because of the nature of this invention it is considered that it is best more fully explained with reference to the accompanying drawing in which:

The FIGURE illustrates in a diagrammatic manner the presently preferred manner or mode of practicing the invention.

DETAILED DESCRIPTION

In the preferred manner of practicing the invention a transducer 10 capable of providing a variable electric signal in response to physical movement such as a variable capacitor as described in the copending application entitled "VARIABLE CAPACITORS" referenced in the preceding is located adjacent to the throat area (not separately numbered) of an individual. Other known transducers can be used instead of this transducer. This transducer 10 is positioned so that an elongated, movable, rigid arm 12 serving as an actuator for the transducer 10 extends so as to physically engage the skin where the soft tissue immediately adjacent to and above the suprasternal notch 14 of an individual is located as indicated diagrammatically in the drawing.

The transducer 10 is preferably held in this position by positioning an attached mounting plate 16 against the skin immediately adjacent to an individual's sternum 18, also as diagrammatically indicated. The plate 16 may be easily held in place against the sternum 18 by virtually any conventional means such as, for example, through the use of adhesive tape 20 as indicated in a diagrammatic manner.

In essence in the preferred manner of practicing the invention the sternum 18 is used as essentially an immobile reference base for use in mounting the transducer 10 so that the actuator 12 may be independently moved in accordance with variation of skin tension as the individual breathes. Although there will be some minor movement of the plate 16 during such breathing in general such movement will normally be so minor as not to significantly interfere with the production of an electric signal from the transducer 10 which reasonably reflects intrathoracic pressure.

In the structure illustrated in the drawing this plate 16 is connected to the transducer 10 through the use of several rigid arms 22 and conventional frictional type universal joints 24 so that once the plate 16 is located on the sternum 18 the transducer 10 can be adjusted to a position as described in which it is relatively fixed and immobile relative to the suprasternal notch 14. The use of the arms 22 and the joints 24 is considered preferable because they permit adjustment so that the indicated structure can be utilized with various different individuals of various different physical dimensions. It is to be understood, however, that a specific apparatus can be constructed in which the transducer 10 is rigidly connected to an appropriate mounting such as the plate 16.

In order for the transducer 10 to be effective for its intended purpose the actuating arm 12 must move in order to accurately reflect changes in the surface tension of the soft tissue adjacent to the super sternal notch 14. This can be accomplished by directly securing the arm 12 to the skin through the use of an appropriate conventional adhesive (not shown). This type of expedient is not considered to be particularly desirable because it is considered that it is simpler and just as effective to utilize a transducer such as the transducer 10 which is internally constructed so as to resiliently bias the arm 12 against the area of the body noted.

The particular transducer described in the copending application entitled "VARIABLE CAPACITORS" identified in the preceding is considered quite desirable in this regard in that it is constructed so that the elements of it which are operative from an electrical standpoint as a variable capacitor serve to automatically bias the arm 12 against the skin and tissue identified in the preceding in such a manner that as an individual breathes the changes in the surface tension of such skin and tissue actuate the transducer 10 so that the transducer 10 provides an electrical output through wires 26 which reasonably reflect such surface tension.

The particular transducer 10 described in this copending application is considered quite desirable in providing such an output which does not reflect changes in the body position or skin movement other than are related to the surface tension of the soft tissue immediately adjacent to the suprasternal notch 14. This is because in the transducer 10 the arm 12 and the electrically operative components which provide the output signal are mounted by a resilient helical spring in a gimbal like manner. This enables what may be loosely referred to as body motion other than that related to changes in the surface tension of the soft tissue adjacent to the suprasternal notch 14 not to be significantly reflected in the electrical output from the transducer 10.

As a consequence of this the individual whose intrathoracic pressure is being measured can breathe normally without the body being especially immobilized in any way while the individual is in an appropriate position such as a prone, resting position. This is considered to contribute to the comfort of the person whose intrathoracic pressure is being measured. As indicated in the noted copending application entitled "VARIABLE CAPACITORS" an exposed collar portion (not illustrated) of the transducer 10 may even be located directly against the body in the area of the superasternal notch so as to support the actuator 10 in contact with the tissue noted. When this is done the normal body movement does not significantly affect the electrical output obtained.

In accordance with the presently preferred practice of the present invention such an output is provided through wires 26 from the transducer 10 to what may be referred to as an electrical package 28 including various known electronic and/or electrical components. This package 28 may be used to provide an output either to operate a conventional meter 30, to operate a conventional light source 32 at varying loads of illumination, or to operate a conventional speaker 34 to provide tones of various frequencies in order to indicate a measurement corresponding to the intrathoracic pressure of the individual.

No effort is made herein to describe the various individual components of the package 28 inasmuch as they are considered to be of a known character. Such components correspond to circuit components as are described in the U.S. Pat. No. 4,063,550 issued Dec. 28, 1977 entitled "METHOD AND APPARATUS FOR TREATING BRONCHIAL ASTHMA." Such components also correspond to circuit components as are described in the U.S. Pat. No. 4,074,710 issued Feb. 21, 1978, entitled "INTRATHORACIC PRESSURE BIOFEEDBACK METHOD", (Application Ser. No. 690,851). In the interest of brevity the entire disclosures of these patents are incorporated herein by reference. It is considered that it is well within the scope of routine electronics to design a wide variety of different specific circuits using different components which will convert any sort of an electrical output from any sort of transducer corresponding to the transducer 10 so as to provide a final output capable of operating a conventional meter 30, a light source 32, or a speaker 34 or the like so that any such item is operated to provide an output serving as a measurement of intrathoracic pressure.

It is believed that the simplicity of the method described herein is a clearcut indication of the desirability of the method. In essence the transducer 10 is employed as a pressure displacement device which cooperates with the super sternal notch 14 in such a manner that the suprasternal notch 14 acts as a diaphragm. The method described in effect measures a change in skin and tissue tension in the body which corresponds to tension changes in the chest cavity as reflected above the pleural membrane. As a result of the mechanism of the measurement involved here it is possible to accurately gauge the work of breathing of an individual suffering from an obstructive lung ailment or problem and to accurately gauge the compliance of the respiratory tract. It will, of course, be recognized that the latter is related to the volume of air moved during inhalation and exhalation.

The method described in this specification is also considered to be especially desirable because this method may be carried out while an individual breathes normally. Thus, in the practice of this method an individual does not have to breathe against an apparatus which tends to interfere with exhalation so as to increase the pressure of the exhaled gases. In other words, an individual in exhaling as the method described herein is practiced need only provide internal body pressure to force exhaled gases from the mouth and need not internally provide additional pressure to force the exhaled gases from the mouth against any resistance to air flow such as might be provided by an external measuring apparatus.

Further the method described herein is considered significant in that the measurement obtained is an electric signal which directly corresponds to changes in surface tension of tissue as noted in the preceding. As a consequence of this the chances of the signal being erroneous due to errors such as might be caused by measuring changes in surface tension by another manner such as pneumatically or through pressure are minimized with the described method.

I claim:

1. The method of obtaining a measurement corresponding to the intrathoracic pressure within the body of an individual which comprises the steps of:

mounting a transducer having a movable actuator so that said transducer is held in place and is supported by the skin immediately adjacent to the sternum and so that said movable actuator is located against the soft tissue of the suprasternal notch of the individual in a position in which variation of the surface tension of the skin occurring during breathing will be transmitted to the actuator and the transducer;

allowing the individual to breathe normally; and monitoring the output of the transducer so as to obtain an output which corresponds to the intrathoracic pressure of an individual as the individual breathes.

2. A method as claimed in claim 1 wherein:

said actuator is resiliently biased against the soft tissue of the suprasternal notch.

* * * * *